United States Patent [19]

Sivak et al.

[11] Patent Number: 4,970,329
[45] Date of Patent: Nov. 13, 1990

[54] SILYL DERIVATIVES OF 2-ALLYL PHENOL

[75] Inventors: Andrew J. Sivak, Edgewood Boro; Leonard A. Cullop, Hempfield Township, Westmoreland County, both of Pa.

[73] Assignee: Aristech Chemical Corporation, Pittsburgh, Pa.

[21] Appl. No.: 405,245

[22] Filed: Sep. 11, 1989

Related U.S. Application Data

[63] Continuation-in-part of Ser. No. 257,895, Oct. 14, 1988, which is a continuation-in-part of Ser. No. 47,960, May 8, 1987, abandoned.

[51] Int. Cl.$^5$ .............................. C07F 7/08; C07F 7/18
[52] U.S. Cl. ................................................... 556/486
[58] Field of Search ......................................... 356/486

[56]  References Cited

U.S. PATENT DOCUMENTS

| | | | |
|---|---|---|---|
| 2,611,778 | 9/1952 | Speer | 556/486 |
| 3,083,219 | 3/1963 | Anderson | 556/486 V X |
| 3,489,783 | 1/1970 | Sheppard et al. | 556/486 X |
| 4,783,495 | 11/1988 | Pastor et al. | 556/48 X |
| 4,920,021 | 5/1990 | Kötysch et al. | 556/486 X |

FOREIGN PATENT DOCUMENTS

| | | | |
|---|---|---|---|
| 0001190 | 1/1985 | Japan | 556/486 |
| 0023384 | 2/1985 | Japan | 556/486 |

OTHER PUBLICATIONS

PCT International Publication Number WO88/08856 (Also Identified as International Application Number PCT/US87/03454), Sivak et al., "Incorporation of Functional Groups in Polymers", Nov. 17, 1988, pp. 1–56.

"High Molecular Weight Polysilanes with Phenol Moieties", Horiguchi et al., Macromolecules, vol. 21, No. 2, 1988, pp. 304–309.

*Primary Examiner*—Paul F. Shaver
*Attorney, Agent, or Firm*—William L. Krayer

[57]  ABSTRACT

Silyl derivatives of 2-allyl phenol include compositions of the formula

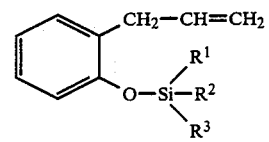

where $R^1$, $R^2$ and $R^3$ are independently selected from alkyl and phenyl groups having up to about twelve carbon atoms. They may be made by silylating the corresponding hydroxyl compound. They are useful as comonomers for olefins to introduce functional sites by Ziegler-Natta catalyst systems.

6 Claims, No Drawings

SILYL DERIVATIVES OF 2-ALLYL PHENOL

RELATED APPLICATION

This is a continuation-in-part of our co-pending application Ser. No. 257,895 filed Oct. 14, 1988, entitled "Incorporation of Functional Groups in Polymers", which is a continuation-in-part of our now abandoned application Ser. No. 047,960 filed May 8, 1987, also entitled "Incorporation of Functional Groups in Polymers"; the entire specification and claims of both applications are incorporated herein by reference.

TECHNICAL FIELD

This invention relates to new silyl derivatives of a certain substituted phenol, specifically to silyl derivatives of 2-allyl phenol. In particular, it relates to compositions of the formula

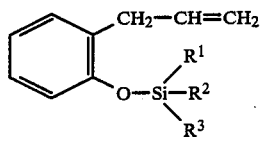

wherein $R^1$, $R^2$ and $R^3$ are independently selected from linear, branched, and cyclic hydrocarbon groups having from one to about eight carbon atoms.

BACKGROUND ART

In European Patent Application No. 86900936.1 (see corresponding PCT International Publication No. WO88/08856, Nov. 17, 1988) and our co-pending patent application Ser. No. 257,895, it is disclosed that comonomers for propylene may be made by protecting the oxygen of a copolymerizable hydroxy-containing compound by substituting the hydrogen thereof with a silyl group having a minimum steric bulk, i.e., at least about three carbon atoms surrounding it.

The compound 2-allyl phenol is known.

Silylated monomers of the general formula

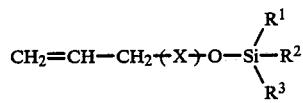

where $-(X)-$ may be a divalent connecting group, are suggested in our above-mentioned co-pending application as comonomers for propylene for the introduction of functional sites to copolymers made by Ziegler-Natta catalysis.

The peculiar advantage of 2-allyl phenol as a potential comonomer in its silylated form apparently has not been seen in the prior art; it is believed this comonomer is novel as a composition of matter.

DISCLOSURE OF INVENTION

The invention herein is a series of new compounds of the formula

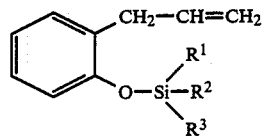

where $R^1$, $R^2$ and $R^3$ are independently selected from linear, branched, and cyclic hydrocarbon groups having from one to about eight carbon atoms. It includes (2-allyl) phenoxy triisopropyl silane, (2-allyl) phenoxy dimethyl phenyl silane, (2-allyl) phenoxy diphenyl methyl silane, (2-allyl) phenoxy trimethyl silane, and (2-allyl) phenoxy triethyl silane.

Following are examples of the preparation of compounds which fall within the above general formula.

EXAMPLE 1

Synthesis of (2-allyl) phenoxy trimethyl silane

All manipulations were performed under inert atmosphere using standard Schlenk techniques. All liquid reagents and solvents were purged with inert gas prior to their introduction into the reaction system. 58.36g (0.435 mol) of 2-allyl phenol was added to a 1000 ml round bottom flask with an argon inlet followed by 150 ml of toluene. The mixture was cooled to 0° C. and 10.07g (0.438 mol) sodium chunks were added in three aliquots. The cold bath was removed one-half hour after the final sodium addition. The formation of NaCl precipitate eventually caused the mixture to stop stirring and therefore after two hours, 50 ml of tetrahydrofuran were added. The mixture stirred at room temperature overnight.

425 ml of heptane were then added and the precipitate was allowed to settle out over a period of two hours. The mixture was filtered through fritted glass with Celite and produced a clear, gold solution. The low boiling components were removed by atmospheric distillation up to a temperature of 120° C. Vacuum distillation of the resultant solution yielded a major component which was distilled at 130–132° C. (2 mm Hg). The collected product represented a 63% yield and were characterized by $^1$H NMR and gcms.

EXAMPLE 2

The synthetic method described in Example 1 was used to prepare (2-allyl) phenoxy tri-iso-propyl silane.

EXAMPLE 3

The synthetic method described in Example 1 was used to prepare (2-allyl) phenoxy diphenylmethyl silane.

Standard inert atmosphere techniques were used to exclude moisture and oxygen throughout the manipulations recited below for copolymerization of monomers such as those described above with lower olefins such as propylene.

A round bottom flask fitted with a side arm, magnetic stirring bar and a stopper, which apparatus had been assembled hot from a drying oven and was then either evacuated and refilled with inert gas several times or (and) purged with the inert gas for at least 15 minutes, was charged with a given amount of solvent, heptane or toluene, usually 125 ml. The solvents were freshly distilled from sodium and triethyl aluminum (TEA) over which they had been refluxing for at least 18 hours under an inert atmosphere. Immediately after the solvent had been charged to the flask alkyl aluminum co-catalyst, which was in the form of a heptane solution of about 25 wt% (0.715 g/ml in heptane), was also added to the flask which was then lowered into a thermostated oil bath and magnetic stirring was begun.

At this point the inert gas atmosphere in the flask was replaced with the gaseous comonomer (propylene or ethylene) by a minimum of 3 cycles of evacuation and refilling back to atmospheric pressure with the comonomer. After the third cycle, the solution was stirred for at least 10 minutes (usually longer) to allow the solvent to become saturated with the comonomer. Pressure was maintained at about one atmosphere via a bubbler.

Next were added an "external donor", which usually was diphenyl dimethoxy silane or phenyl triethoxy silane, if one was being used, and the other comonomer. The polymerization was initiated by the addition of the transition metal containing co-catalyst, which was a titanium tetrachloride on a magnesium chloride support.

As the gaseous comonomer was consumed it was replaced by maintaining the pressure constant at one atmosphere via a bubbler.

After a predetermined period of time (generally about two hours) the reaction was quenched by the addition of acidified alcohol (HCl in iso-propanol, ethanol, and/or methanol). The quenched reaction slurry was combined with the alcohol solution of volume at least twice the original volume of the inert reaction solvent. The resultant slurry was stirred for at least 45 minutes and then filtered. This treatment not only stopped the reaction, it dissolved catalyst residues and removed the silyl groups and thus regenerated the hydroxyl groups.

If the filtration proceeded very slowly, the slurry was combined with enough water to make the filtration proceed at a convenient rate.

The polymer was resuspended in alcohol, stirred, filtered and vacuum dried overnight. Boiling heptane soluble content was determined by standard methods.

EXAMPLE 4

Propylene and (2-allyl) phenoxy trimethyl silane copolymerization

A 500 ml round bottom flask which was fitted with a sidearm was evacuated and refilled with argon three times. To this flask were added 125 ml of dry, degassed heptane followed by 3.8 ml (0.018 mol) of (2-allyl) phenoxy trimethyl silane. The solution was subsequently saturated with propylene and 5.3 ml of the triethylaluminum co-catalyst (0.715 g/ml in heptane) was injected into the flask.

This mixture was then lowered into an oil bath which was maintained at 50° C. and 0.095g of the titanium co-catalyst (which served to initiate the polymerization) were added. The reaction proceeded over a period of two hours and was subsequently quenched by the addition of approximately 300 ml of acidified isopropanol. Stirring of this alcoholic suspension continued for approximately one hour followed by filtration of the product and resuspension of the polymer in isopropanol with stirring for one-half hour. The product was then filtered and vacuum dried.

We claim:

1. A compound of the formula

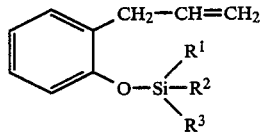

in which $R^1$, $R^2$ and $R^3$ are independently selected from linear, branched, and cyclic hydrocarbon groups having from one to about eight carbon atoms.

2. (2-allyl) phenoxy triisopropyl silane.
3. (2-allyl) phenoxy dimethyl phenyl silane.
4. (2-allyl) phenoxy diphenyl methyl silane.
5. (2-allyl) phenoxy trimethyl silane.
6. (2-allyl) phenoxy triethyl silane.

* * * * *

UNITED STATES PATENT AND TRADEMARK OFFICE
CERTIFICATE OF CORRECTION

PATENT NO. : 4,970,329

DATED : November 13, 1990

INVENTOR(S) : Andrew J. Sivak and Leonard A. Cullo

It is certified that error appears in the above-identified patent and that said Letters Patent is hereby corrected as shown below:

On the title page, item [75]:
Under "Inventors:", change "Leonard A. Cullop" to -- Leonard A. Cullo --.

Column 1, line 35, change "86900936.1" to -- 88900936.1 --.

Column 2, line 9, change "independentlY" to -- independently --.

Signed and Sealed this

Eighth Day of September, 1992

Attest:

DOUGLAS B. COMER

Attesting Officer     Acting Commissioner of Patents and Trademarks